United States Patent
Dahl et al.

(10) Patent No.: US 7,178,480 B2
(45) Date of Patent: Feb. 20, 2007

(54) METHOD OF REDUCING RISK OF INFECTION OF A BOVINE TEAT AFTER CESSATION OF MILKING

(76) Inventors: Janet F. Dahl, P.O. Box 2944, Oshkosh, WI (US) 54903; Dennis L. Edison, E. 18861 City. Rd. D, Fall Creek, WI (US) 54742; Paul E. Fowler, P.O. Box 2944, Oshkosh, WI (US) 54903; Michael R. Stettler, 960 HoneyCreek Rd., Oshkosh, WI (US) 54909

( * ) Notice: Subject to any disclaimer, the term of this patent is extended or adjusted under 35 U.S.C. 154(b) by 0 days.

(21) Appl. No.: 11/122,074

(22) Filed: May 5, 2005
(Under 37 CFR 1.47)

(65) Prior Publication Data
US 2005/0208148 A1     Sep. 22, 2005

Related U.S. Application Data

(63) Continuation of application No. 10/859,977, filed on Jun. 4, 2004, now Pat. No. 6,935,271, which is a continuation of application No. 09/976,745, filed on Oct. 13, 2001, now Pat. No. 6,752,102, which is a continuation-in-part of application No. 09/406,040, filed on Sep. 27, 1999, now Pat. No. 6,302,058.

(51) Int. Cl.
*A01J 7/04*     (2006.01)

(52) U.S. Cl. .................................... 119/14.47; 119/670
(58) Field of Classification Search ............. 119/14.47, 119/670, 604, 603, 651, 673, 652; 222/190, 222/635, 636, 209, 207, 212
See application file for complete search history.

(56) References Cited

U.S. PATENT DOCUMENTS 2,532,088 A     11/1950     Cordis (Continued)

OTHER PUBLICATIONS

Benjamin Carroll, Journal of Bacteriology, 69:413-417 (1955).

(Continued)

*Primary Examiner*—Yvonne R. Abbott
(74) *Attorney, Agent, or Firm*—Kenyon & Kenyon LLP

(57) ABSTRACT

A method of reducing infection of a bovine teat is described. This method may include providing a surfactant for reducing infection of a bovine teat, creating a foam with a mixture of surfactant and compressed gas, extracting milk from the teat of a bovine, and, following cessation of milking the teat, placing the foamed surfactant on the teat from which milk was extracted. In some instances the foamed surfactant may form a bead at an end of the teat. The method may further include using a compressor to compress the gas, leaving the foam on the teat for more than one minute, and using a hand-held teat cup that can massage the teat as the foam is applied.

7 Claims, 4 Drawing Sheets

U.S. PATENT DOCUMENTS

| | | |
|---|---|---|
| 3,713,423 A | 1/1973 | Sparr, Sr. |
| 3,728,449 A | 4/1973 | Cantor et al. |
| 3,828,776 A | 8/1974 | Sparr, Sr. |
| 3,874,561 A | 4/1975 | Zackheim et al. |
| 3,917,119 A | 11/1975 | Kahn |
| 3,921,860 A | 11/1975 | Zackheim |
| 4,012,504 A | 3/1977 | Eckols |
| 4,049,830 A | 9/1977 | Pugliese |
| 4,305,346 A | 12/1981 | Sparr, Sr. |
| 4,759,931 A | 7/1988 | van Paassen |
| 4,928,857 A * | 5/1990 | Ecker .................... 222/211 |
| 4,970,992 A | 11/1990 | Aiken |
| 5,269,444 A | 12/1993 | Wright |
| 5,368,868 A | 11/1994 | Winicov |
| 5,379,724 A | 1/1995 | Dee et al. |
| 5,529,770 A | 6/1996 | McKinzie et al. |
| 5,534,266 A | 7/1996 | Ricketts |
| 5,535,700 A | 7/1996 | Boudreau |
| 5,570,819 A | 11/1996 | Uehira et al. |
| 5,616,348 A | 4/1997 | Winicov |
| 5,641,498 A | 6/1997 | Loosemore |
| 5,651,977 A | 7/1997 | Kross |
| 5,720,984 A | 2/1998 | Ricketts |
| 5,722,350 A | 3/1998 | Marshall |
| 5,776,479 A | 7/1998 | Pallos et al. |
| 6,348,206 B1 * | 2/2002 | Ricketts ................ 424/405 |
| 6,544,539 B1 * | 4/2003 | Ricketts ................ 424/405 |
| 6,644,240 B1 * | 11/2003 | Dietrich ................ 119/14.47 |
| 6,895,892 B2 * | 5/2005 | Sellner et al. .......... 119/14.54 |
| 6,935,270 B2 * | 8/2005 | Wipperfurth et al. ...... 119/670 |

OTHER PUBLICATIONS

"McCutcheon's Emulsifiers and Detergents," 1987.

\* cited by examiner

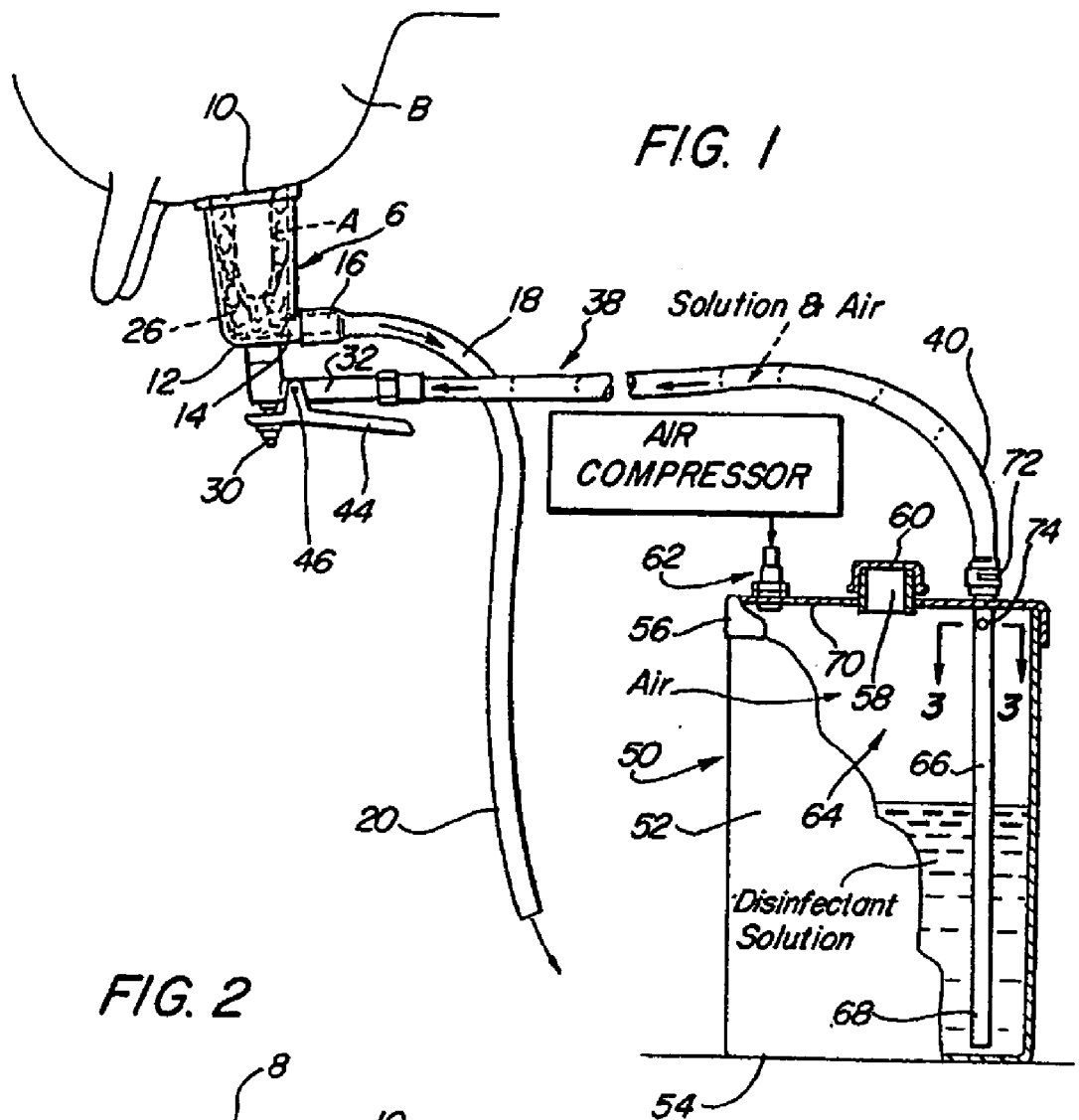

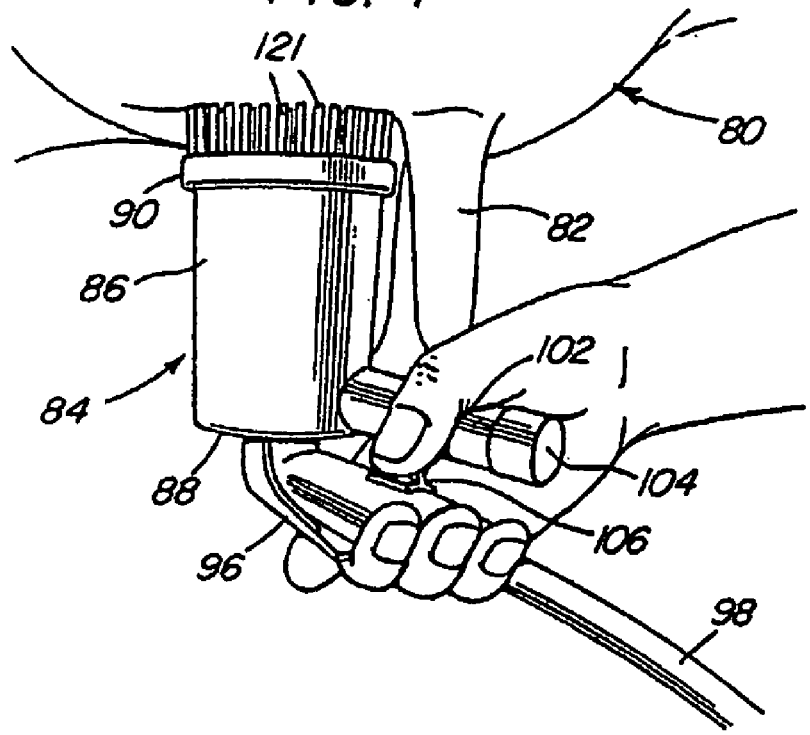
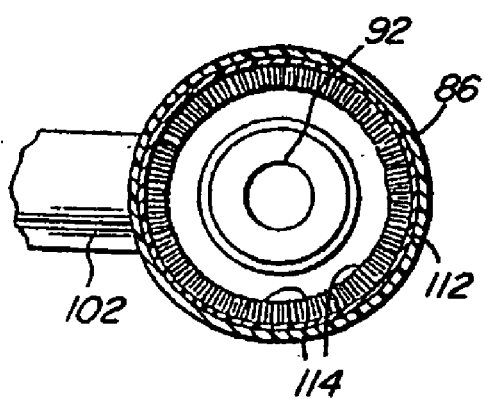
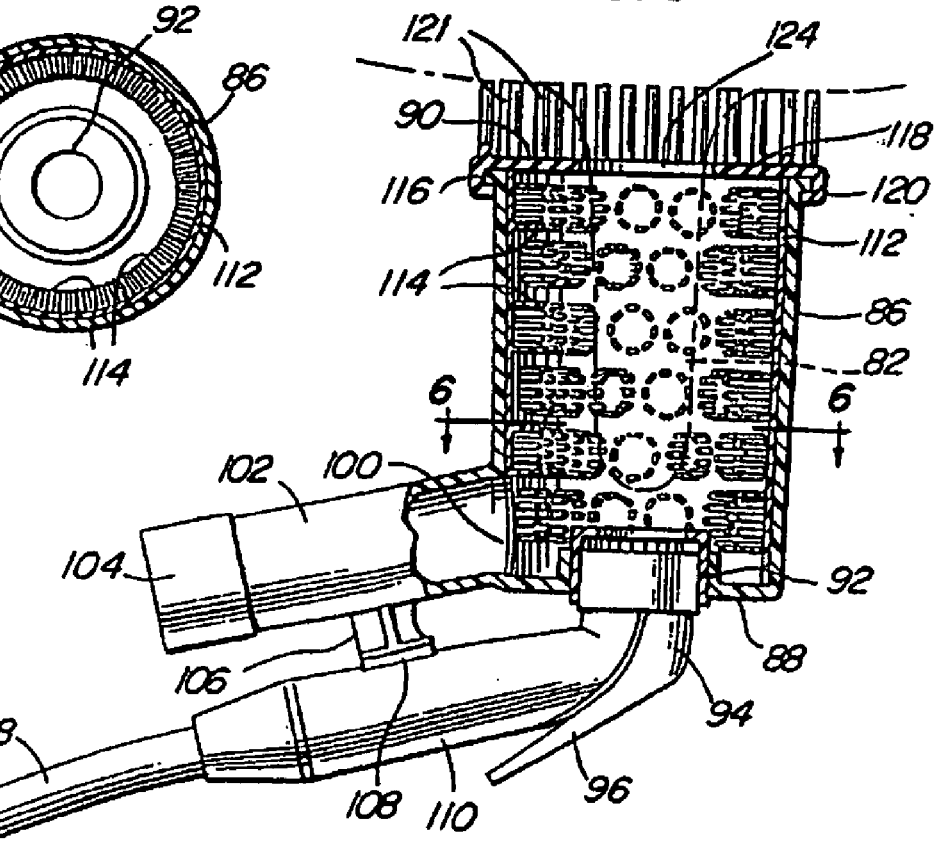

METHOD OF REDUCING RISK OF INFECTION OF A BOVINE TEAT AFTER CESSATION OF MILKING

RELATED APPLICATIONS

This application is a Continuation of application Ser. No. 10/859,977, filed Jun. 4, 2004, now U.S. Pat. No. 6,935,271 which is a continuation of application Ser. No. 09/976,745, now U.S. Pat. No. 6,752,102 B2, which has a filing date of Oct. 13, 2001, and a grant date of Jun. 22, 2004, which is a Continuation-in-part of application Ser. No. 09/406,040, now U.S. Pat. No. 6,302,058, which has a filing date of Sep. 27, 1999, and a grant date of Oct. 16, 2001.

BACKGROUND OF THE INVENTION

This invention relates to a new and improved methods and apparatus for producing a foam surfactant containing a biocide, germicide, disinfectant, etc., as a bovine teat dip, teat wash and post dip.

Surfactant liquids and applicators are well known for use as bovine teat dips, and typical publications concerning these applicators are found in U.S. Pat. Nos. 3,713,423 and 4,305,346. Publications concerning bovine teat dips include U.S. Pat. Nos. 5,534,266 and 5,720,984 the latter patent disclosing a non-ionic, laureth (11–16) carboxylic acid surfactant teat dip and hand foam which is highly suitable for use in this invention. Publications concerning bovine teat dip formulations are U.S. Pat. Nos. 3,728,449; 4,012,504; 4,049,830; 4,759,931; 5,529,770; 5,641,498; 5,368,868; 5,534,266; 5,616,348; 5,651,977; and 5,720,984. Polyethenoxy detergents and I.sub.2 are disclosed in an article by Benjamin Carroll in the Journal of Bacteriology, 69: 413–417, (1955). A PVP surfactant for a teat dips is also suitable, and so is one sold by Norman Fox & Co. under the trade name of NORFOX-P9, and listed in "McCutcheon's Emulsifiers and Detergents", 1989 (incorporated herewith) specifically for use with iodophors. Other types of teat dips are sold as Klenzade™ Teat Guard containing a nonyl phenoxypolyethoxy ethanol surfactant and titratable iodine. U.S. Pat. No. 5,616,348 supra, discloses a polyethoxylated polyoxypropylene block copolymer (Poloxamer) and iodine which is suitable as a bovine teat dip.

It would be highly desirable to provide a foamed bovine teat dip which would cover the outer teat area, and provide protection to the teat canal when the teat sphincter is open following a milking procedure, when the teat canal is exposed and highly vulnerable to immediate infection. Even when the teat sphincter has closed, it would still be desirable to prevent infection from reaching the area of the teat opening, and the teat area in general, with reduced run off.

This would enable the foam to adhere to and remain in close and protective contact with the teat. Further, it is desired to provide an apparatus with the capability of producing foam using a wide variety of surfactants, such as those disclosed, supra.

U.S. Pat. Nos. 3,713,423 and 4,305,346 describe an apparatus which coats a bovine teat area with fine mist or spray, but these patented devices are hand operated and do not produce any foam, let alone a foam fulfilling the above protective characteristics. It will also be appreciated that use of foam reduces the amount of surfactant used for a bovine teat dip by about one-half compared to either a spray or liquid dip, and hence an improvement in the operation of these two patents is desirable.

SUMMARY OF THE CLAIMED INVENTION

A method of reducing infection of a bovine teat is described. This method may include providing a surfactant for reducing infection of a bovine teat, creating a foam with a mixture of surfactant and compressed gas, extracting milk from the teat of a bovine, and, following cessation of milking the teat, placing the foamed surfactant on the teat from which milk was extracted. In some instances the foamed surfactant may form a bead at an end of the teat. The method may further include using a compressor to compress the gas, leaving the foam on the teat for more than one minute, and using a hand-held teat cup that can massage the teat as the foam is applied.

BRIEF DESCRIPTION OF THE DRAWINGS

FIG. 1 is a view of the overall apparatus as set up for use, and showing how it is used and constructed and illustrating in section various parts of a tank for containing a solution of surfactant;

FIG. 2 is an enlarged view of parts in section and elevation detailing the container cup and component parts associated therewith;

FIG. 3 is a cross section on a slightly enlarged scale taken approximately on the plane of the section line 3—3 of FIG. 1;

FIG. 4 is a fragmentary, perspective view of a cow udder with the milk 'let down' stimulating apparatus of the instant invention operatively associated therewith;

FIG. 5 is an enlarged, fragmentary side elevation view of FIG. 4 and with major portions being broken away and illustrated in vertical section;

FIG. 6 is a horizontal sectional view taken along lines 6—6 of FIG. 4;

BRIEF DESCRIPTION OF THE PREFERRED EMBODIMENTS

Figure 7:
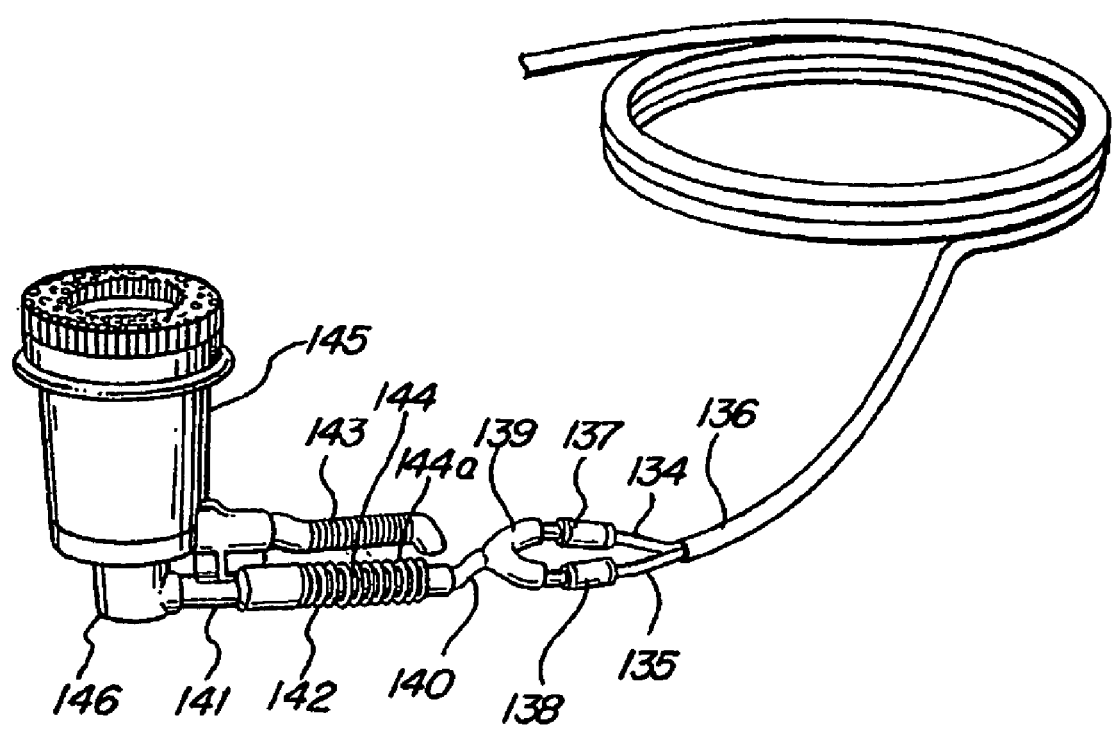
FIG. 7 is a perspective view of an improved system for producing foam.

A teat cup 6 is shown in FIGS. 1 and 2 is provided with the required depth and cross sectional dimension to accommodate a teat A on an udder B. The teat cup 6 has an open top or mouth portion 8 and surrounded by a suitable udder contacting bead 10. This beaded mouth adapts to the required contact with the part of the udder immediately encompassing the teat A. The bottom of the cup 12 is provided on one side with a laterally projecting drainage or emptying neck 14, and an end portion 16 of a drainage and fluid disposal hose 18 detachably secured thereto.

The discharge end 20 of the fluid disposal hose may be placed in a collecting device (not shown) or discharged to sewage, or in the case of foam, the emptying neck 14 may be closed off entirely. The bottom portion of the cup is provided with a valve 22 having a body 24 depending below the bottom 12 of the cup and the upper end of the valve leads to an opening 25 (about 1" in diameter) at the bottom of the cup.

When a pressurized mixture of air (or $CO_2$, $N_2$, etc.) and surfactant enters this inlet fluid expansion bore, the mixture expands from an initial pressurized value down to atmospheric pressure, to become a foam 26 in the cup, thereby making adhering contact with the teat and surrounding udder.

The valve body 22 provides an intake line coupling 32 having a suitable bore, and which controls the on-off delivery of disinfectant surfactant to valve body 24, the line coupling being connected through a coupling 34 to a flow and line mixer 38 which supplies surfactant under pressure to the cup 6 to produce the foam 26. A useful internal line diameter of the line mixer 38 is about ¼", and employing pressure conditions, as detailed infra, a useful length of the mixer line 38 is about 20–30 feet.

The intake line coupling 32 also serves as a gripping member and carries a manually trippable lever 42. The lever is provided with a handle portion 44 suitably shaped opposed to the line coupling 32 and having ears 46 straddling and pivotally connected to the coupling; the lever has a fork 48 connected with the line coupling 32 for opening and closing the valve.

A tank 50 having a sidewall 52 and bottom 54 is provided for containing disinfectant surfactant for supply to the teat cup 6. A flanged cover 56 and cap 60 is mounted centrally of the tank through which the tank can be filled, and a valve 62 functions to connect with a supply of air pressure governed by an air regulator (not shown) for pressuring air into the interior of the tank 64.

A liquid lifting pipe 66 extending from line 38 has an inlet 68 near the bottom of the tank, the lifting pipe being connected by a clamp 72 to line 38. Preferably, inlet 68 has a restricted opening or is otherwise provided with a restrictor (not shown) to prevent excessive intake of surfactant. A plurality e.g., four orifices 74 about {fraction (1/16)}" in diameter (shown in FIG. 3) are formed on the lifting pipe 66 to provide for adequate mixing of air and surfactant, thereby producing a drier foam and also reducing the consumption of surfactant.

Compressed air is supplied at an air pressure of about 20–100 psi (preferably 80–100 psi) through intake valve 62 and fed into the space 64 of the tank 50. The compressed air compresses surfactant into the inlet 68 of the lifting pipe 66. Also, compressed air in the space 64 enters the four orifices 74 where it mixes and is entrained with the surfactant in the lifting pipe 66; the pressurized mixture of surfactant and entrained air then passes into the flow and line mixer 38. Upon entering the valve 22 and the inlet fluid expansion bore 25 at the bottom of the cup 6, the pressurized mixture of air and surfactant is depressurized down to atmospheric or ambient, which converts the mixture into the teat dip foam 26. Water is usually added to the surfactant to produce the desired foam consistency.

The foam produced by the apparatus of this invention is unique in terms of functioning as a bovine teat dip since it adheres to the teat and udder area without significant run off, and forms a bead at the end of the teat. This area of the teat is at significant risk to infection both prior to and subsequent to milking, and the presence of the bead considerably reduces the possibility of infection. Also, since there is little foam runoff, a longer period of protection is afforded against bacterial infection.

Moreover, following cessation of milking, use of a post-dip which is not wiped off, enables the open teat sphincter to be covered by the foam bead (with significant protection for about ten minutes), when the open sphincter and hence the teat canal are at a high risk of infection.

A preferred teat cup for use in the present invention is shown in FIGS. 4–6, and illustrates a cow udder 80 and dependent teats 82. A teat apparatus 84 for washing and milk 'let-down' includes an upwardly opening cup 86 including a bottom wall 88 and open upper end 90. The bottom wall 88 includes a central inlet fluid expansion bore 92 into which is fitted the outlet end of a nozzle 94, infra, for upwardly discharging foam. The nozzle 94 includes an actuating lever 96 and a surfactant flow and mixer line 98 which is coupled to the nozzle for continuously supplying cleaning foam to the cup.

The lower portion of the cup 86 includes a lateral outlet 100 about which the inlet end of a drain neck 102 and a closure cap 104 are secured, the drain neck including a downwardly projecting support 106 carrying a downwardly opening abutment 108 at its lower end against which the main body portion 110 of the nozzle 94 may be upwardly abutted.

The interior of the cup 86 is lined with a sleeve 112 of resilient material and the sleeve includes circumferentially and axially spaced groups of inwardly projecting flexible blade type elements 114 projecting radially inwardly from the outer periphery of the cup 86, and the open upper end 90 of the cup includes a circumferentially extending and outwardly projecting ridge 116. The blade type elements 114 are sized to be of greater length than width, and greater width than thickness.

An annular partial top wall 118 is provided and includes a down-and-in-turned peripheral attaching snap fitting flange 120 over the upper end 124 of the cup 80, and the partial top wall includes a plurality of circumferentially and radially spaced axially projecting resilient fingers 121 which upwardly abut the underside portions of the udder 80 immediately surrounding an associated teat 82.

During a cleaning operation, the central inlet fluid expansion bore 92 is utilized to upwardly dispense cleaning foam into the bottom of the cup 86, and the foam not only contacts an associated centrally disposed teat 82, but also contacts and moves the blade elements 114. This movement causes the blade elements to vibrate or laterally oscillate, thereby performing a scrubbing action on the teat exterior.

Additionally, the resilient fingers 121 upwardly abut and stimulate those portions of the udder 80 immediately surrounding the upper base portion of an associated teat 82. Also, some of the upwardly directed foam from the nozzle 94 passes upwardly through the upper end 124 and further stimulates the udder, similar to the tongue of a nursing calf.

Another equally important function of the blade elements and fingers is to force and uniformly distribute the foam around and into contact with the immersed teat. Also, the blade elements and fingers force the foam upwardly to the top portion of the cup. Hence, any dirt on the teat is removed and forced upwardly by the foam to the top of the cup and then is discarded. This results in a very clean cup for succeeding foam dip applications in subsequent milking operations.

Although the apparatus described in FIGS. 1–6 produces a suitable quality of foam, it has been found that air and the foam forming liquid have a tendency to separate in the flow and line mixer, causing the foam to collapse. This in turn requires that extra foam forming surfactant and liquid be sent into the line in order to restore lost ingredients. It has now been found that if better mixing takes place before the mixture enters the teat cup, upon expansion, greater control is possible when producing the foam. Typically, mixing takes place in the nozzle, and the mixture is then further expanded upon entering the teat cup at ambient or atmospheric pressure. However, it may also be advantageous to mix the air and liquid upstage of the nozzle in place of, or in addition to mixing at the nozzle.

Accordingly, an improved apparatus is shown in FIG. 7 for producing a combined teat and udder dip and a teat wash and post teat dip, comprising means for separately feeding air and foam forming liquid, including surfactant into a mesh or equivalent component, such as an orifice, contained in the nozzle. The mesh component enables intimate mixing of air and a foamable solution, generally containing surfactant, to form an initial compressed mixture. In the second stage of mixing, the compressed mixture is further mixed at the nozzle, and then forwarded to the teat cup where it expands to a foam at atmospheric pressure.

This two stage mixing enables a better overall control of foam production, with less waste and spillage. Also, less foamable solution is required for producing an effective amount of foam compared to the use of liquid teat dips or spray.

As shown in FIG. 7, a solution of surfactant and germicide is fed to a line 134, and air from a compressor is fed to a separate line 135 wrapped in a plastic coating 136 such as nylon, dacron, PVC, polypropylene, polyethylene, etc. The plastic coating material is selected based on a combination of durability, flexibility, tangle-free performance, and appearance.

The surfactant solution and compressed air from their respective lines 134 and 135 are fed through check valves 137 and 138 which are used to prevent backflow and also to effect an initial mixing, and the compressed air and surfactant solution streams are combined into a single stream in flow connector 139. The single stream from the flow connector is then fed through a short lead 140 into an on-off control nozzle 141 constructed of a suitable plastic material to ensure non-reactivity with iodine. The control nozzle 141 is secured to a teat cup 145 through a polypropylene adaptor 146 feeding an expansion bore in the teat cup described, supra.

The control nozzle includes spring-loaded handles 142, 143 which are used to release to the teat cup a mixture of air and a solution of liquid and germicides including iodine and iodine compounds such as iodophors, chlorine dioxide, and chlorine, or bacteriostats such as quaternary ammonium compounds and chlorhexidine. When the handles are closed together, the mixture of surfactant and air are expanded to a foam in the expansion bore of the teat cup 145, as described supra, thereby producing foam; when the handles are released, the spring loading will turn off the control nozzle. As shown, the lead 140 connects the single stream of surfactant and compressed air into the handle 142 where they are intimately mixed by a plastic mesh 144 such as polytetrafluorethylene (TEFLON.sup.®) which is secured within a loose spring coil 144a inserted inside the handle. TEFLON.sup.® is the preferred material since it is fairly inert to iodine. If desired, the TEFLON.sup.® mesh may be inserted into the lead 140, or the flow connector 139, and/or the handle 142.

Figure 8:
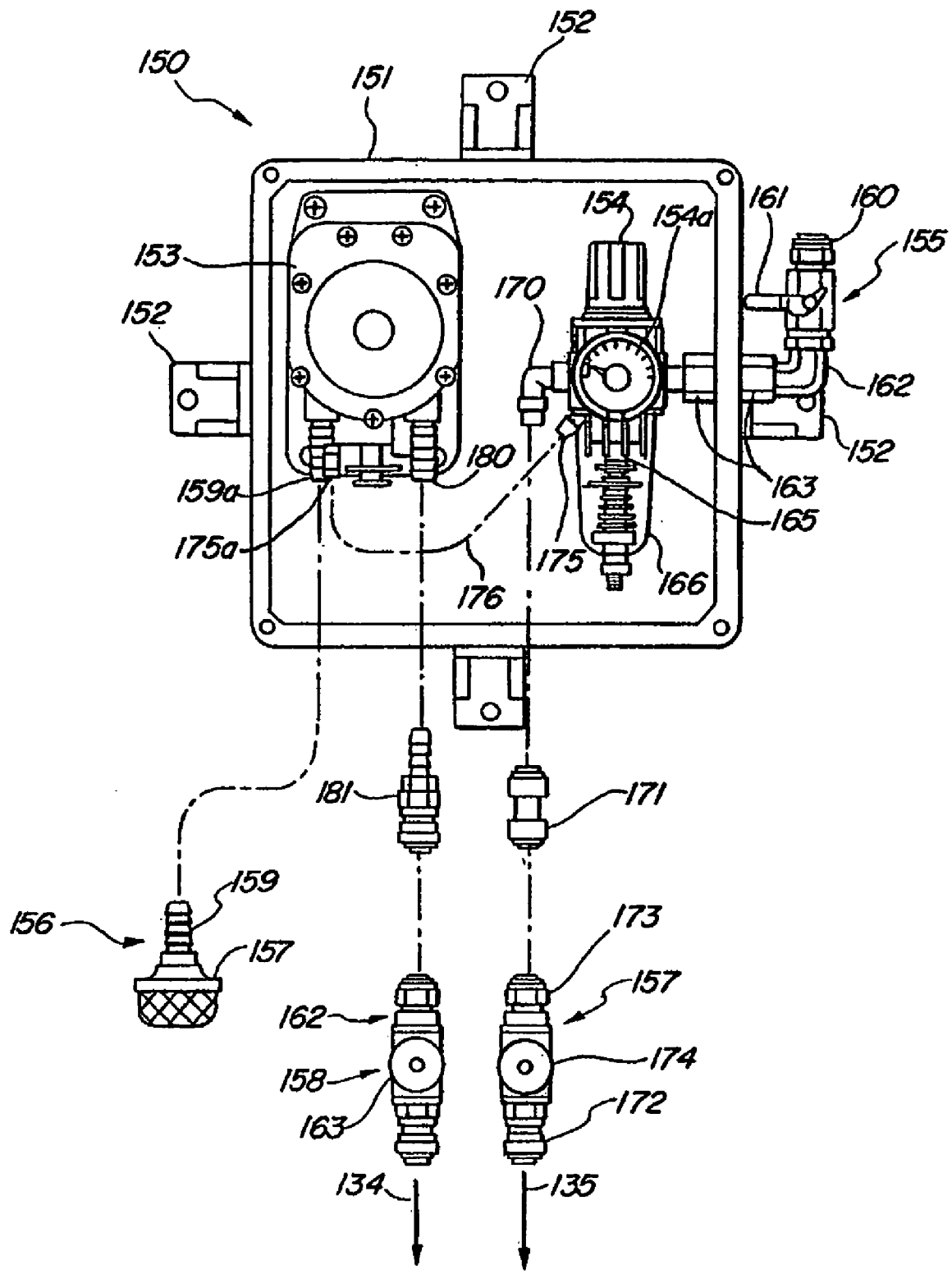
FIG. 8 is a diagrammatic view of another embodiment of an apparatus of this invention for producing foam.

FIG. 8 illustrates a control system 150 for use in conjunction with a large container size of foam forming liquid, say for containers of drum size quantity. The control system 150 is contained in a housing 151 shown with the cover removed, and the control system is mounted to a suitable fixture by mounting feet 152. The control system includes a liquid pump 153, air intake regulator/filter 154, monitoring gauge 154a, an air intake piping 155, a liquid intake line 156 an air outlet line 157 and a liquid outlet line 158.

Air from a compressor is fed into an air intake line 160 which is controlled by an on-off valve 161 and passes through an elbow 162 and adaptor 163 to the air pressure gauge 154a which monitors the regulator/filter unit 154. A second air filter 165 encased in a replacement bowl 166 augments filter unit 154.

A portion of the air is passed from the pressure gauge 154a and regulator/filter unit 164 through an elbow connector 170 and adaptor 171 to a hose line connector 172 via a connector 173 and valve 174. The hose line connector 172 feeds the air line 135 shown in FIG. 7. Excess air from the pressure gauge 154a and regulator/filter unit 154 is shunted to the liquid pump 153 via a barb elbow 175 connected to a pump hose barb 175a, through a line 176, and this excess air powers the liquid pump.

Liquid surfactant and germicide is removed from a container by the liquid pump 153 through the intake line 156 which includes a strainer 157 and a hose barb 159 which connects to a pump hose barb 159a and is then pumped out through hose barb connectors 180 and 181. Connection is made with the liquid line 134 shown in FIG. 7 using a connector 162 and valve 163.

The average herd life of cows is three to about seven years, as noted in U.S. Pat. Nos. 5,534,266 and 5,720,984 and during the period when use of the present equipment commenced in 1999 to the present time, no discernable adverse repercussions in herd life were observed.

It will be appreciated that other germicides besides iodine, HI, I.sup.−, I.sub.2, and iodophors may be used in conjunction with the foam formed by the apparatus of this invention, and they include chlorine dioxide, and chlorine; bacteriostats such as chlorhexidine; and, quaternary ammonium compounds are also suitable. Additionally, ingredients such as foaming agents and thickeners may be utilized to improve foam forming capabilities of the surfactant when combined with air.

What is claimed is:

1. A method of reducing infection of a bovine teat comprising:
   providing a surfactant for reducing infection of a bovine teat;
   creating a foam with a mixture of surfactant and compressed gas
      wherein the foam is created in a hand-held teat cup as the compressed gas and surfactant mixture expands upon being exposed to ambient pressure;
   extracting milk from the teat of a bovine; and
   following cessation of milking the teat, placing the foamed surfactant on the teat from which milk was extracted.

2. The method of claim 1 wherein the foamed surfactant, placed on the teat from which the milk was extracted, forms a bead at an end of the teat.

3. The method of claim 1 wherein the compressed gas is supplied by a compressor.

4. The method of claim 1 wherein the foamed surfactant placed on the teat remain on the teat for more than one minute.

5. A method of reducing infection of a bovine teat comprising:
   providing a surfactant for reducing infection of a bovine teat;
   creating a foam with a mixture of surfactant and compressed gas;
   extracting milk from the teat of a bovine; and
   following cessation of milking the teat, placing the foamed surfactant on the teat from which milk was extracted,
      wherein a sphincter of the teat is open when the foamed surfactant is placed on the teat.

6. The method of claim 1 wherein the hand-held teat cup contains blade elements that vibrate or oscillate when the teat cup surrounds a teat and foam is being created within the teat cup.

7. A method of reducing infection of a bovine teat comprising:
   providing a surfactant for reducing infection of a bovine teat;
   creating a foam with a mixture of surfactant and compressed gas;
   extracting milk from the teat of a bovine; and
   following cessation of milking the teat, placing the foamed surfactant on the teat from which milk was extracted.
   wherein the compressed gas is supplied by a compressor,
   wherein the compressor supplies compressed gas at more than 80 psi.

* * * * *